US00PP29136P2

(12) United States Plant Patent
Heemskerk

(10) Patent No.: US PP29,136 P2
(45) Date of Patent: Mar. 20, 2018

(54) ***HEMEROCALLIS* PLANT NAMED 'VER00322'**

(50) Latin Name: ***Hemerocallis* hybrid**
Varietal Denomination: VER00322

(71) Applicant: Gerardus J. C. M. Heemskerk, Noordwijk (NL)

(72) Inventor: Gerardus J. C. M. Heemskerk, Noordwijk (NL)

( * ) Notice: Subject to any disclaimer, the term of this patent is extended or adjusted under 35 U.S.C. 154(b) by 0 days.

(21) Appl. No.: 15/530,033

(22) Filed: Nov. 21, 2016

(51) Int. Cl.
*A01H 5/02* (2006.01)

(52) U.S. Cl.
USPC ..... Plt./312

(58) Field of Classification Search
USPC ..... Plt./263.1, 312
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Hemerocallis* named 'VER00322' that is characterized by its flowers that are dark red in color with yellow throats and distinct yellow midribs on the petals, its everblooming habit; blooming from the end of June to October in The Netherlands, and its dormant plant habit.

2 Drawing Sheets

Botanical classification: *Hemerocallis* hybrid.
Cultivar designation: 'VER00322'.

BACKGROUND OF THE INVENTION

The present invention relates to a new and distinct cultivar of *Hemerocallis* plant of hybrid origin, botanically known as *Hemerocallis* 'VER00322' and will be referred to hereafter by its cultivar name, 'VER00322'.

The new cultivar was developed through on on-going breeding program conducted by the Inventor in Noordwijk, The Netherlands. The objectives of the breeding program are to develop new cultivars of *Hemerocallis* that are everblooming with compact plant habits in a range of flower colors.

The new cultivar arose from crosses made in summer of 2006. Proprietary seed parent lines were pollinated with a mixture of pollen collected from proprietary pollen parents and the collected seeds were pooled and sown for evaluation. 'VER00322' was selected as a single unique plant from the resulting seedlings in summer of 2009. The specific parents are unknown and none of the possible parent plants are named or patented.

Asexual propagation of the new cultivar was first accomplished by division in Noordwijk, The Netherlands in 2009 by the Inventor. Asexual propagation by division and tissue culture initiated with meristem tissue has determined that the characteristics of this cultivar are stable and are reproduced true to type in successive generations.

SUMMARY OF THE INVENTION

The following traits have been repeatedly observed and represent the characteristics of 'VER00322'. These attributes in combination distinguish 'VER00322' as a new and distinct cultivar of *Hemerocallis*.

1. 'VER00322' exhibits flowers that are dark red in color with yellow throats and distinct yellow midribs on the petals.

2. 'VER00322' exhibits an everblooming habit; blooming from the end of June to October in The Netherlands.
3. 'VER00322' exhibits a dormant plant habit.

The new cultivar can be most closely compared to the *Hemerocallis* cultivars 'VER00198' (U.S. Plant Pat. No. 27,004) and *Hemerocallis* 'VER00157' (U.S. Plant Pat. No. 28,484). 'VER00198' is similar to 'VER00322' in having flowers with a single color and having a light colored midrib on the petals, in having a dormant plant habit and an extended flowering period. 'VER00198' differs from 'VER00322' in having a flowers that are pink in color, an earlier blooming period and flowers that are more round in shape due to broader sepals. 'VER00157' is similar to 'VER00322' in having a light colored midrib on the petals, in having a dormant plant habit and an extended flowering period. 'VER00157' differs from 'VER00322' in having a shorter plant height, leaves that are lighter green in color, and flowers that are pink in color and more round in shape due to broader sepals.

BRIEF DESCRIPTION OF THE DRAWINGS

The accompanying colored photographs illustrate the overall appearance and distinct characteristics of the new *Hemerocallis*. The photographs were taken of a 2 year-old plant of the new cultivar as grown in a 12-liter container in a greenhouse under normal light in Noordwijk, The Netherlands.

The photograph in FIG. 1 provides a side view of 'VER00322' in bloom.

Figure 1:
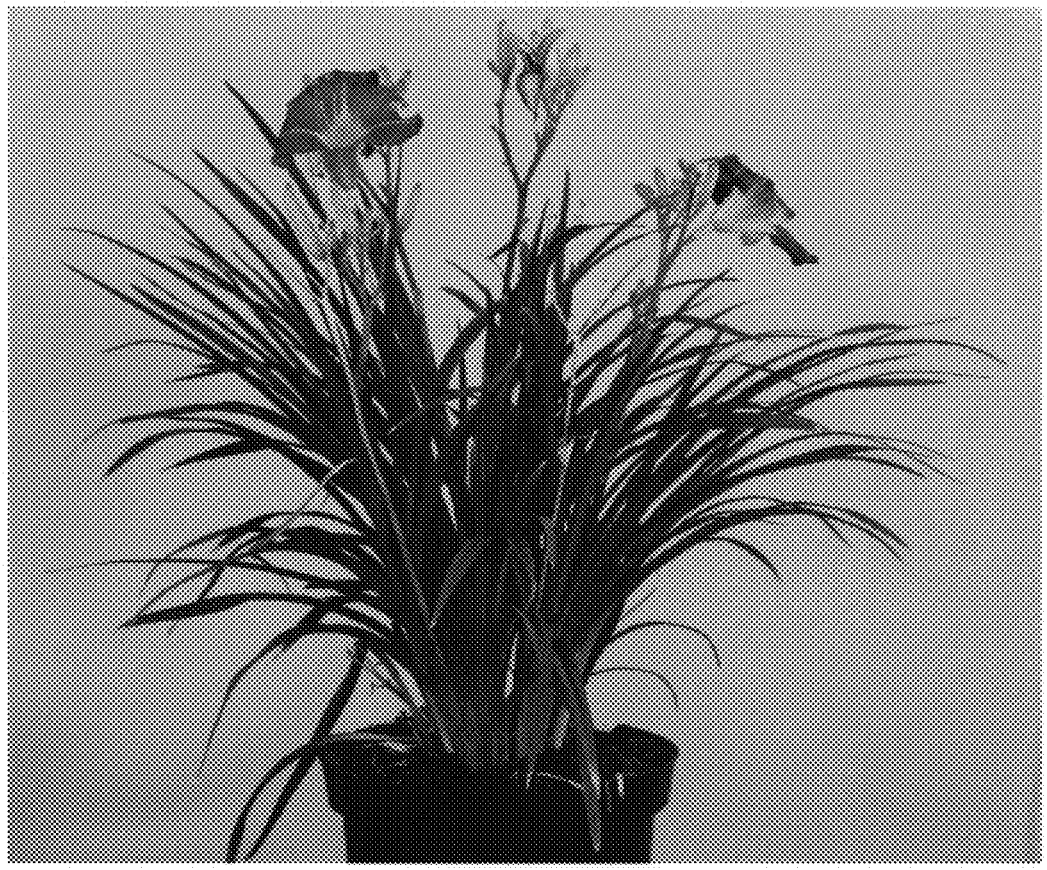
Figure 2:
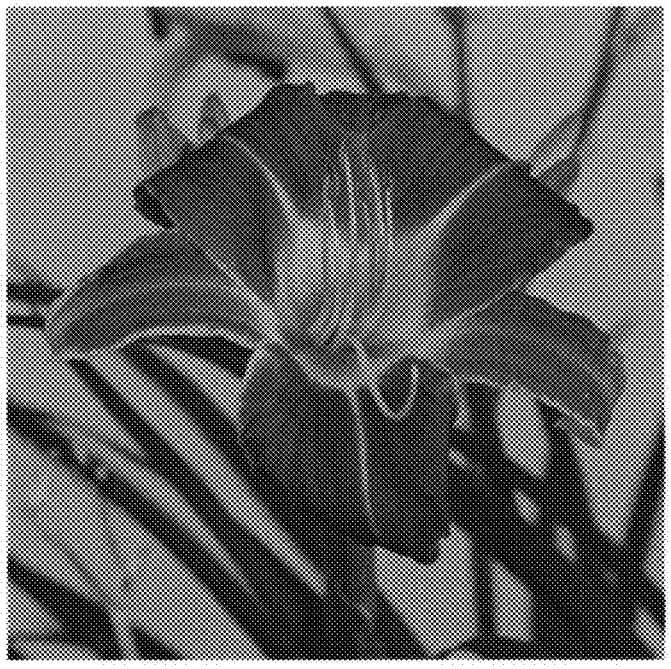

The photograph in FIG. 2 provides a close-up view of a flower of 'VER00322'.

Figure 3:
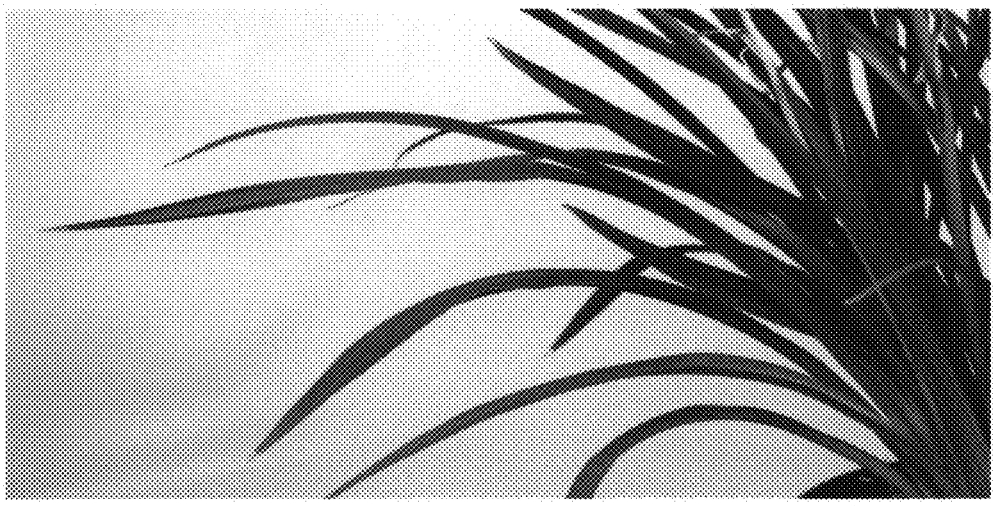

The photograph in FIG. 3 provides a close-up view of the foliage of 'VER00322'.

The colors in the photographs are as close as possible with the digital photography and printing techniques utilized and the color codes in the detailed botanical description accurately describe the new *Hemerocallis*.

DETAILED BOTANICAL DESCRIPTION OF THE PLANT

The following is a detailed description of 2 year-old plants of the new cultivar as grown in a 12-liter container in a greenhouse under normal light in Noordwijk, The Netherlands. The plants were grown under average day temperatures of 16° C. to 28° C. and average night temperatures of 10° C. to 14° C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period*.—End of June to October in The Netherlands.

*Plant type*.—Herbaceous perennial.

*Plant habit*.—Upright, broad spreading with flowers held above the foliage, dormant type.

*Height and spread*.—Reaches about 50 cm in height and spread (2 year-old plant in the landscape).

*Hardiness*.—At least in U.S.D.A. Zones 5 to 11.

*Diseases*.—No susceptibility or resistance has been observed.

*Root description*.—Fleshy with fibrous secondary roots.

*Propagation*.—Division and tissue culture.

*Root development*.—Approximately 4 months from propagation to potted plant, approximately 8 months for bare root field production from single divisions.

*Growth rate*.—Moderate.

Foliage description:

*Leaf shape*.—Linear.

*Leaf division*.—Simple.

*Leaf base*.—Decurrent.

*Leaf apex*.—Long acuminate with a short apiculate outer tip.

*Leaf venation*.—Parallel, color upper surface; 143A, color lower surface; 137A.

*Leaf margins*.—Entire.

*Leaf attachment*.—Decurrent, no petioles.

*Leaf arrangement*.—Basal shoots, equitant.

*Leaf orientation*.—Held upright, carinate, curved.

*Leaf surface*.—Both surfaces glabrous, smooth and matte.

*Leaf color*.—Young leaves upper and lower surface; color between 143A and 146A, mature leaves upper surface; between NN137A and 147A, covered with a thin waxy layer 189B in color, mature leaves lower surface; 137B.

*Leaf size*.—Up to 55.2 cm in length, an average of 1.3 cm in width.

*Leaf quantity*.—Average of 13 per shoot.

Flower description:

*Inflorescence type*.—Scape bearing a panicle of single flowers, freely flowering.

*Inflorescence size*.—An average of 12.5 cm in height (excluding peduncle), 17.2 cm in diameter.

*Lastingness of flowers*.—About 24 hours, self cleaning.

*Flower size*.—An average of 10.9 cm in height, 11.3 cm in diameter, 10.2 cm in depth, flower throat 7 mm in diameter, flower tube 2.2 cm in length, flower tube 6 mm in diameter.

*Flower fragrance*.—None.

*Flower shape*.—Campanulate.

*Flower number*.—Average of 14, varying between 6 and 23.

*Flower aspect*.—Upright to outward.

*Flower bud*.—Oblanceolate in shape, average of 5.2 cm in length and 9 mm in diameter, smooth, glabrous, moderately glossy, color 150B, base 144C, tip 143A.

*Rate of flower opening*.—Approximately 10% of flowers open at a time, average of 8 weeks for all flowers to open per scape.

*Flower attachment*.—Petiolate.

*Petals*.—3, 1 whorl, oblanceolate in shape, average of 11.9 cm in length and 4.5 cm in width, upper surface smooth, matte and velvety, lower surface smooth, very slightly glossy and glabrous, margins entire, apex obtuse, base fused into tube (lower 18.5%), color of upper surface when opening and fully open; between 178A and 183B, fading to 14A, margins 14C, striped from base to tip 14A to 14B, color of lower surface when opening; 15B to 15C, margins 173B to 173C.

*Sepals*.—3, 1 whorl, rotate, campanulate in arrangement, average of 11.5 cm in length, 2.6 cm in width, oblanceolate in shape, entire margins, base is 25% fused, acute apex, upper and lower surfaces, matte, smooth and glabrous, color upper surface when opening and fully open; 179A, fading to a color in between 22A and 26A with base 14A, color lower surface when opening and fully open; 20A in color.

*Calyx*.—Campanulate in shape, average of 7.2 cm in length and 11.1 cm in diameter.

*Peduncles*.—Both surfaces smooth, glabrous and matte, strong, held at an average angle of 10°, 52.2 cm in length, 6 mm in diameter, 143A to 144A in color, covered with a very thin waxy layer 189B in color.

*Pedicels*.—Surface is smooth, glabrous and matte, strong, held at an average angle of 45°, 9 mm in length, 3 mm in diameter, a color between 141B to 143A in color.

Reproductive organs:

*Gynoecium*.—Pistil; 1, average of 10.3 cm in length, style; 10.25 cm in length, 21A in color, stigma; crested, 0.5 mm in length and diameter, 14A in color, ovary; 143A to 143B in color.

*Androecium*.—Stamens; 6, anthers; dorsifixed and narrow oblong in shape, 7 mm in length and 200A to 203A in color; filament; 6.4 cm in length, 23B in color, pollen; abundant in quantity and 17A in color.

*Fruit/seeds*.—None observed.

It is claimed:

1. A new and distinct cultivar of *Hemerocallis* plant named 'VER00322' as herein illustrated and described.

* * * * *